United States Patent
Cha

(10) Patent No.: US 11,830,626 B2
(45) Date of Patent: *Nov. 28, 2023

(54) SYSTEM AND METHOD FOR IMPROVING THE SPEED OF DETERMINING A HEALTH RISK PROFILE OF A PATIENT

(71) Applicant: Healthcare Interactive, Inc., Glenwood, MD (US)

(72) Inventor: Henry H. Cha, Glenelg, MD (US)

(73) Assignee: Healthcare Interactive, Inc., Glenwood, MD (US)

( * ) Notice: Subject to any disclaimer, the term of this patent is extended or adjusted under 35 U.S.C. 154(b) by 78 days.

This patent is subject to a terminal disclaimer.

(21) Appl. No.: 17/175,007

(22) Filed: Feb. 12, 2021

(65) Prior Publication Data

US 2021/0241917 A1 Aug. 5, 2021

Related U.S. Application Data

(63) Continuation of application No. 15/866,412, filed on Jan. 9, 2018, now Pat. No. 10,923,232.

(51) Int. Cl.
*G16H 50/30* (2018.01)
*G16H 10/60* (2018.01)
(Continued)

(52) U.S. Cl.
CPC ............. *G16H 50/30* (2018.01); *G06F 40/30* (2020.01); *G06F 40/58* (2020.01); *G16H 10/60* (2018.01);
(Continued)

(58) Field of Classification Search
CPC ... G16H 10/00–80/00; G06F 1/00–2221/2153; G06Q 10/00–2250/905
See application file for complete search history.

(56) References Cited

U.S. PATENT DOCUMENTS 6,182,029 B1  1/2001 Friedman
6,915,254 B1  7/2005 Heinze et al.
(Continued)

FOREIGN PATENT DOCUMENTS

JP  2014-512624 A  5/2014

OTHER PUBLICATIONS

International Search Report and Written Opinion dated Apr. 10, 2019 for PCT Application No. PCT/US2019/012883.
(Continued)

*Primary Examiner* — Jonathon A. Szumny
(74) *Attorney, Agent, or Firm* — Plumsea Law Group, LLC

(57) ABSTRACT

In one aspect, the present disclosure is directed to a method for improving the speed of determining a health risk profile associated with a patient. The method may include the step of retrieving patient medical information about the patient, wherein the patient medical information is an uncoded natural language expression in a first language. The method may also include comparing the patient medical information with records in a first database. If the patient medical information matches the preselected medical information, the method includes performing a first data conversion procedure. If the patient medical information fails to match any record in the first database, the method includes performing a second data conversion procedure, wherein the first data conversion procedure is performed faster than the second data conversion procedure.

12 Claims, 16 Drawing Sheets

(51) Int. Cl.

| | | |
|---|---|---|
| *G16H 50/20* | (2018.01) | |
| *G06F 40/30* | (2020.01) | |
| *G06F 40/58* | (2020.01) | |
| *G16H 20/90* | (2018.01) | |
| *G06Q 50/22* | (2018.01) | |
| *G06Q 40/08* | (2012.01) | |

(52) U.S. Cl.
CPC .............. *G16H 50/20* (2018.01); *G06Q 40/08* (2013.01); *G06Q 50/22* (2013.01); *G16H 20/90* (2018.01)

(56) References Cited

U.S. PATENT DOCUMENTS

| | | |
|---|---|---|
| 7,555,425 B2 | 6/2009 | Oon |
| 7,624,027 B1 | 11/2009 | Stern et al. |
| 7,945,462 B1 | 5/2011 | Goral |
| 8,056,118 B2 | 11/2011 | Piliouras |
| 8,655,668 B2 | 2/2014 | Heinze |
| 8,930,226 B1 | 1/2015 | Kerr |
| 10,042,979 B2 | 8/2018 | Moore et al. |
| 2004/0249667 A1 | 12/2004 | Oon |
| 2012/0136646 A1 | 5/2012 | Kraenzel et al. |
| 2012/0271612 A1 | 10/2012 | Barsoum et al. |
| 2013/0226608 A1 | 8/2013 | Di Lascia et al. |
| 2014/0379374 A1 | 12/2014 | Vinals |
| 2015/0088548 A1 | 3/2015 | Charlot et al. |
| 2015/0310455 A1 | 10/2015 | Vinals |
| 2016/0048758 A1* | 2/2016 | Campbell ............ G06F 40/289 706/46 |
| 2016/0267232 A1 | 9/2016 | Koll |
| 2016/0350486 A1 | 12/2016 | Plunkett et al. |
| 2017/0177822 A1 | 6/2017 | Fogel |
| 2017/0185893 A1 | 6/2017 | Wetta |
| 2017/0235884 A1 | 8/2017 | Harmon et al. |
| 2017/0357771 A1 | 12/2017 | Connolly et al. |
| 2018/0143975 A1 | 5/2018 | Casal et al. |
| 2018/0374581 A1 | 12/2018 | Berringer et al. |

OTHER PUBLICATIONS

International Search Report and Written Opinion dated May 23, 2019 for Application No. PCT/US2019/012888.

Office Action dated Dec. 12, 2019 in U.S. Appl. No. 15/866,415.

International Preliminary Report on Patentability dated Jul. 23, 2020 in PCT Application No. PCT/US2019/012883.

Final Office Action dated Jun. 18, 2020 in U.S. Appl. No. 15/866,415.

Zheng et al., "Web-based Real-Time Case Finding for the Population Health Management of Patients With Diabetes Mellitus: A Prospective Validation of the Natural Language Processing-Based Algorithm With Statewide Electronic Medical Records," 2016, JMIR Medical Informatics, vol. 4, Issue 4, e37, pp. 1-13 (Year: 2016).

Office Action dated Oct. 31, 2022 in U.S. Appl. No. 17/175,038.

Final Office Action dated Feb. 10, 2023 in U.S. Appl. No. 17/175,038.

* cited by examiner

INSURANCE CLAIM DATA

| ENTRY | ID | PATIENT ID | MZ ENTER DATE | CONDITIONS | BILL AMOUNT |
|---|---|---|---|---|---|
| 1 | 2458787 | 1255 | 2016-01-31 10:26:48.000 | 偏头痛 | 570.00 |
| 2 | 9087452 | 1255 | 2016-02-06 10:17:36.000 | 脑梗塞 / 感冒 | 469.10 |
| ⋮ | ⋮ | ⋮ | ⋮ | ⋮ | ⋮ |
| ⋮ | ⋮ | ⋮ | ⋮ | ⋮ | ⋮ |

FIG. 3

TRANSLATED INSURANCE CLAIM DATA

| ENTRY | ID | PATIENT ID | MZ ENTER DATE | CONDITIONS | BILL AMOUNT |
|---|---|---|---|---|---|
| 1 | 2458787 | 1255 | 2016-01-31 10:26:48.000 | MIGRAINE | 570.00 |
| 2 | 9087452 | 1255 | 2016-02-06 10:17:36.000 | CEREBRAL INFARCTION/COLD | 469.10 |
| ⋮ | ⋮ | ⋮ | ⋮ | ⋮ | ⋮ |
| ⋮ | ⋮ | ⋮ | ⋮ | ⋮ | ⋮ |

FIG. 4

| | | CODED INSURANCE CLAIM DATA | | | |
|---|---|---|---|---|---|
| PATIENT ID | MZ ENTER DATE | CONDITIONS | CODE | CODE SYSTEM | CODE DESCRIPTION |
| 1 | 2016-01-31 10:26:48.000 | MIGRAINE | G43.909 | ICD-10-CM | MIGRAINE, UNSPECIFIED, NOT INTRACTABLE, WITHOUT STATUS MIGRAINOSUS. |
| 2 | 2016-02-06 10:17:36.000 | CEREBRAL INFARCTION/COLD | I63.9 | ICD-10-CM | CEREBRAL INFARCTION, UNSPECIFIED |
| ⋮ | ⋮ | ⋮ | ⋮ | ⋮ | ⋮ |
| ⋮ | ⋮ | ⋮ | ⋮ | ⋮ | ⋮ |

FIG. 5

COMPREHENSIVE PATIENT CLINICAL PROFILE REPORT 600     PATIENT ID: 1255

| AGE | 26 | SEX | F |
|---|---|---|---|
| PCP ID | | PRODUCT | |

PRIOR COSTS | CASE COMPLEXITY

| TOTAL COST | $50,187 | CHRONIC CONDITION COUNT | 13 |
|---|---|---|---|
| RX COST | $0 | ACTIVE INGREDIENT COUNT 230 | |
| RESOURCE UTILIZATION BAND | 4 | FRAILTY FLAG | N |
| LOCAL ACG CONCURRENT RISK | 12.06 | FRAILTY CONCEPT(S) | |
| | | COMPASSIONATE ALLOWANCE CONDITIONS | N |

PREDICTIVE VALUES | LIKELIHOOD OF HOSPITALIZATION

| RANK PROBABILITY HIGH TOTAL COST | 0.70 | HOSPITAL DOMINANT MORBIDITY TYPES | 0 |
|---|---|---|---|
| PREDICTED TOTAL COST RANGE | $40,000 - $50,000 | PROBABILITY HOSPITAL ADMISSION (6 MOS) | 0.08 |
| | | PROBABILITY HOSPITAL ADMISSION (12 MOS) | 0.12 |
| RANK PROBABILITY HIGH RX COST | 0.57 | PROBABILITY ICU/CCU ADMISSION | 0.03 |
| PREDICTED RX COST RANGE | 240 | PROBABILITY INJURY-RELATED ADMISSION | 0.00 |
| HIGH RISK UNEXPECTED PHARMACY | | PROBABILITY LONG-TERM ADMISSION (12+ DAYS) | 0.02 |
| PROBABILITY OF PERSISTENT HIGH USER | 0.55 | PROBABILITY OF READMISSION | 0.08 |

UTILIZATION | COORDINATION OF CARE

| OUTPATIENT VISITS | 0 | COORDINATION RISK | |
|---|---|---|---|
| ER VISITS 245 | 0 | # UNIQUE PROVIDERS SEEN | |
| INPATIENT ADMISSIONS W/O BIRTH AND INJURY | | # SPECIALTY TYPES SEEN GENERALIST SEEN | |
| UNPLANNED 30-DAY READMISSIONS | | MANAGEMENT VISIT COUNT | |
| INPATIENT DAYS | | % VISITS PROVIDED BY MAJORITY SOURCE OF CARE | |
| MAJOR PROCEDURE PERFORMED | N | CARE DENSITY RATIO | |
| DIALYSIS SERVICE | N | CARE DENSITY QUANTILE | |
| NURSING SERVICE | N | CARE DENSITY EST. COST SAVING | |
| CANCER TREATMENT | N | CARE DENSITY EST. COST SAVING RATIO | |
| PSYCHOTHERAPY SERVICE | N | CARE DENSITY EST. COST SAVING | |
| MECHANICAL VENTILATION | | | |

FIG. 6

COMPREHENSIVE PATIENT CLINICAL PROFILE REPORT
PATIENT ID: 1255

CONDITION PROFILE WITH PHARMACY ADHERENCE MARKERS

| CONDITION | PRESENT? | CSA | MPR | # REFILL | UNTREATED |
|---|---|---|---|---|---|
| COPD | ICD | | | | |
| Chronic Renal Failure | ICD | | | | |
| Depression | ICD | | | | |
| Disorders of Lipid Metabolism | ICD | | | | |
| Hypertension | ICD | | | | |

TREATED CONDITION PROFILE

HIGH IMPACT CONDITIONS
EDC'S
REN01    CHRONIC RENAL FAILURE

MODERATE IMPACT CONDITIONS
EDC'S
MUS03    DEGENERATIVE JOINT DISEASE
NUR03    PERIPHERAL NEUROPATHY, NEURITIS
NUR05    CEREBROVASCULAR DISEASE
RES04    EMPHYSEMA, CHRONIC BRONCHITIS, COPD

LOW IMPACT CONDITIONS
EDC'S
CAR11    DISORDERS OF LIPID METABOLISM
CAR14    HYPERTENSION. W/O MAJOR COMPLICATIONS
EYE07    CONJUNCTIVITIS. KERATITIS
GAS01    GASTROINTESTINAL SIGNS AND SYMPTOMS

FIG. 7

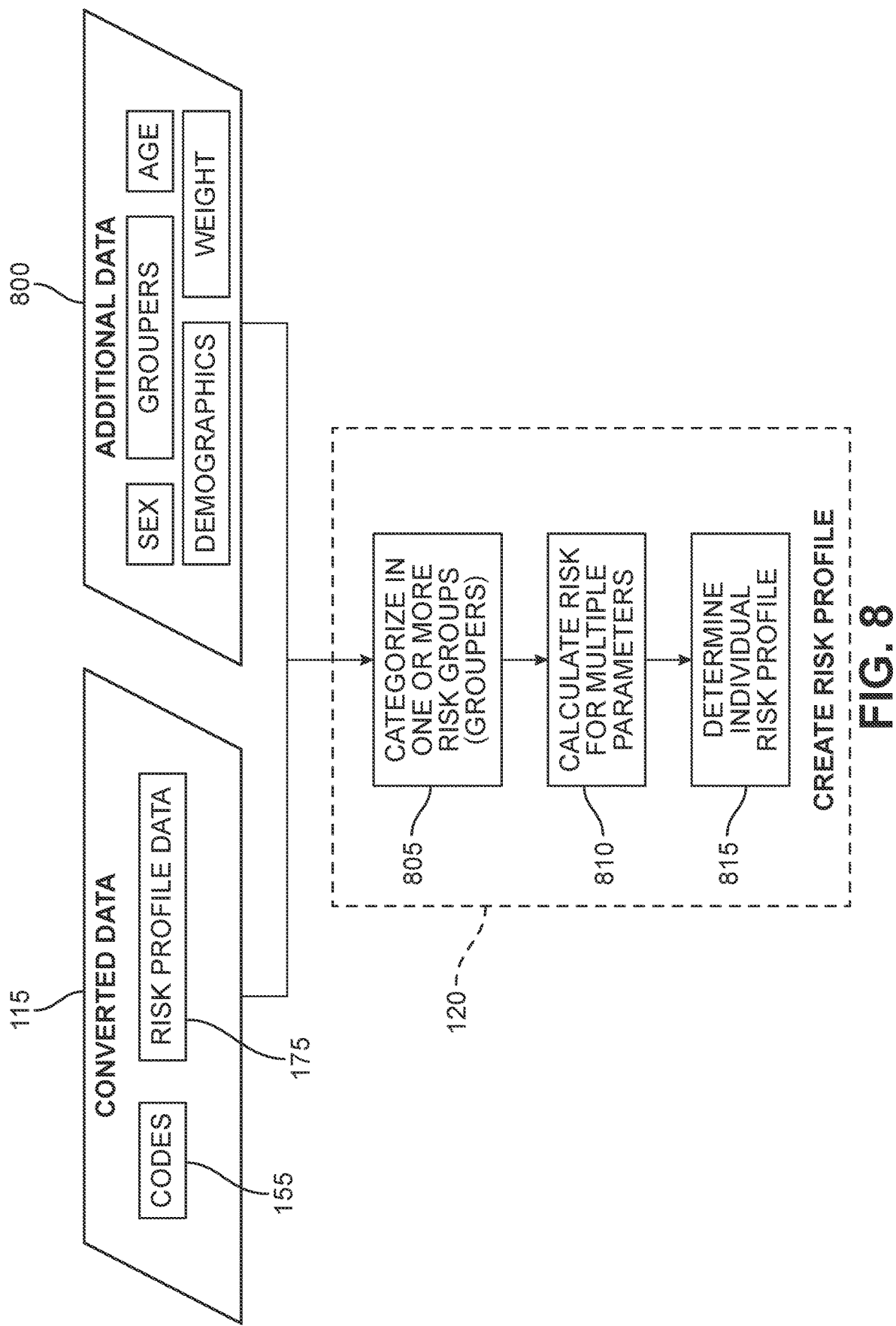

SYSTEM AND METHOD FOR IMPROVING THE SPEED OF DETERMINING A HEALTH RISK PROFILE OF A PATIENT

CROSS-REFERENCE TO RELATED APPLICATIONS

This application is a continuation of Cha, U.S. application Ser. No. 15/866,412, filed Jan. 9, 2018, and entitled "System and Method for Improving the Speed of Determining a Health Risk Profile of a Patient," the entire disclosure of which is incorporated herein by reference.

BACKGROUND

The present disclosure is directed to systems and methods for improving health risk determination and, particularly, to improving the speed of determining a health risk profile of a patient.

In the healthcare industry, patient medical data is collected, analyzed, and used to improve patient care, healthcare resources, and financial considerations associated with the healthcare industry. For example, insurance programs and rates may be customized and budgeted for groups and/or individuals based on patient data.

Patient medical data, such as diagnoses and procedures (e.g., treatments), are used to predict healthcare risk of individual patients based on the individual patients' own data as well as the collective data of a group of patients with whom each patient has something in common. Commonalities between patients may include aspects of the patients' medical histories (e.g., a similar diagnoses and/or treatment) and other patient data such as age, sex, etc., as well as demographics, such as geographic residency, socio-economic status, etc.

Points of commonality are used to group patients for purposes of analyzing their data, and thus, may be referred to as "groupers." Once patient data has been sorted based on one or more groupers, a health risk profile can be created for each individual patient using predictive modeling. The health risk profile can include a plurality of probabilities for various health-related indices. For example, the probability that an individual patient will be admitted to a hospital within a 6 or 12 month period may be calculated. Similarly, a probability that the patient will be a persistent high user of insurance and a probability that the patient will incur a high total cost to insurance may also be determined. One or more health risk indices, such as these, may collectively provide an individual health risk profile for a patient.

Consistency in patient medical information facilitates determining health risk profiles for patients. For example, for two patients diagnosed with the same condition and given the same treatment, predictions based on such patient medical information can be more accurate if the doctors' notes on the reports for these two patients (e.g., for a particular doctor's visit) are identical. Since each doctor is an individual human being, standardized code systems have been developed in which a plurality of predetermined codes are associated with particular medical conditions and treatments. For example, a diagnosis of "type I diabetes" is assigned a diagnosis code. Type II diabetes would have a similar, but different diagnosis code. A prescribed treatment, such as "insulin," is assigned a particular treatment code. A medical code system is adopted by large healthcare systems, for example, in an entire country or collection of countries, in order to provide a level of consistency between diagnoses and treatments across the entire healthcare system that adopts the code system. There are international medical code systems adopted by many countries.

While certain countries and groups of countries have adopted standardized code systems, and international medical code systems have been established, not all countries and geographic regions have adopted such systems. In some countries, the code systems have not yet been adopted because the narrative associated with each predetermined code in the system has not been reliably translated into the native language of the non-adopting countries. In addition, some geographic regions have different diagnoses and treatments than found elsewhere in the world, which are not accounted for in the international code systems. For example, treatments considered to be "alternative" in western societies, such as acupuncture, may not have a treatment code in a given international medical code system.

In countries that have not adopted an international medical code system, creating reliable health risk profiles for patients is more difficult.

SUMMARY

The present disclosure is directed to systems and methods for improving the speed of determining a health risk profile of a patient. The disclosed system is configured to utilize a translation-based data conversion procedure as a foundational process for obtaining the data in a format usable to determine a health risk profile. The system is also configured to perform database updates based on prior data conversion and health risk profile creation. The database is updated with records of associations between foreign language patient medical information and predetermined medical codes. The database may also be updated with records of associations between foreign language patient medical information and health risk indices.

Once the database has been updated sufficiently with respect to certain diagnoses or procedures, creation of health risk profiles based on such diagnoses and procedures may be performed without having to formally translate the patient medical information from the foreign language. That is, the data processing system can convert the foreign language patient medical information directly into a standardized code or directly into a health risk index. By skipping one or more steps in the data conversion process, the data conversion process can be completed much faster, particularly when certain steps in the process must be performed by an outside resource, which may be located in a different location than the health risk profile creation system. In addition, the reliability of the risk profile can be improved due to increased consistency in the patient medical information used to determine the risk profiles.

In one aspect, the present disclosure is directed to a method for improving the speed of determining a health risk profile associated with a patient. The method may include the step of retrieving patient medical information about the patient, wherein the patient medical information is an uncoded natural language expression in a first language. The method may also include comparing the patient medical information with records in a first database, the first database including a plurality of records, wherein at least one record in the first database has unique preselected medical information and a first predetermined code associated with the preselected medical information, and wherein the preselected medical information is also an uncoded natural language expression in the first language. Further, the method may include determining if the patient medical information matches one of the records in the first database by comparing the patient medical information with the preselected medical information of the records in the first database. If the patient medical information matches the preselected medical information, the method includes performing a first data conversion procedure by immediately assigning the first predetermined code associated with the preselected medical information to the patient medical information. If the patient medical information fails to match any record in the first database, the method includes performing a second data conversion procedure by sending the patient medical information to a translation resource, and receiving translated patient medical information from the translation resource, wherein the translated patient medical information is in a second language; sending the translated patient medical information to a coding resource; and receiving, from the coding resource, a second predetermined code associated with the patient medical information. In addition, the method may include determining a health risk profile for the patient using one of the first predetermined code and the second predetermined code, wherein the first data conversion procedure is performed faster than the second data conversion procedure.

In another aspect, the present disclosure is directed to a method for improving the speed of determining a health risk profile associated with a patient. The method may include retrieving patient medical information about the patient, wherein the patient medical information is an uncoded natural language expression in a first language, and comparing the patient medical information with records in a first database, the first database including a plurality of records, wherein at least one record in the first database has unique preselected medical information and a first health risk index associated with the preselected medical information, and wherein the preselected medical information is also an uncoded natural language expression in the first language. The method may also include the step of determining if the patient medical information matches one of the records in the first database by comparing the patient medical information with the preselected medical information of the records in the first database. If the patient medical information matches the preselected medical information, the method includes performing a first data conversion procedure by immediately assigning the first health risk index associated with the preselected medical information to the patient medical information. If the patient medical information fails to match any record in the first database, the method includes performing a second data conversion procedure to convert the patient medical information to a predetermined code associated with the patient medical information. Also, the method may include determining a health risk profile for the patient using one of the first health risk index and the predetermined code, wherein the first data conversion procedure is performed faster than the second data conversion procedure.

In another aspect, the present disclosure is directed to a system for improving the speed of determining a health risk profile associated with a patient. The system may include a processor and a non-transient computer readable medium including instructions for performing a plurality of steps. The steps may include retrieving patient medical information about the patient, wherein the patient medical information is an uncoded natural language expression in a first language and comparing the patient medical information with records in a first database, the first database including a plurality of records, wherein at least one record in the first database has unique preselected medical information and a first predetermined code associated with the preselected medical information, and wherein the preselected medical information is also an uncoded natural language expression in the first language. In addition, the steps may include determining if the patient medical information matches one of the records in the first database by comparing the patient medical information with the preselected medical information of the records in the first database. If the patient medical information matches the preselected medical information, the steps include performing a first data conversion procedure by immediately assigning the first predetermined code associated with the preselected medical information to the patient medical information. If the patient medical information fails to match any record in the first database, the steps include performing a second data conversion procedure by sending the patient medical information to a translation resource, and receiving translated patient medical information from the translation resource, wherein the translated patient medical information is in a second language; sending the translated patient medical information to a coding resource; and receiving, from the coding resource, a second predetermined code associated with the patient medical information. In addition, the steps may include determining a health risk profile for the patient using one of the first predetermined code and the second predetermined code, wherein the first data conversion procedure is performed faster than the second data conversion procedure.

In another aspect, the present disclosure is directed to a method of creating a local risk database for improving the speed of determining a health risk profile associated with a patient. The method may include retrieving patient medical information about a first patient, wherein the patient medical information is an uncoded natural language expression in a first language. The method may also include performing a first data conversion procedure including: sending the patient medical information to a translation resource if there is no match between the patient medical information and the records in the database; receiving translated patient medical information from the translation resource, wherein the translated patient medical information is in a second language; sending the translated patient medical information to a coding resource; and receiving, from the coding resource, a predetermined code associated with the translated medical information. Also, the method may include using the predetermined code to determine a health risk profile for the patient and adding to the database a record of an association between the predetermined code and the patient medical information.

In another aspect, the present disclosure is directed to a method of patient communication based on a health risk profile. The method may include retrieving patient medical information about the patient and determining a health risk profile for the patient based on the retrieved patient medical information. In addition, the method may include producing an automated follow-up with a patient based on the health risk profile.

In another aspect, the present disclosure is directed to a method of patient communication based on a health risk profile. The method may include retrieving patient medical information about the patient and determining a health risk profile for the patient based on the retrieved patient medical information. In addition, the method may include tracking actions of a patient following an office visit and providing the patient with action-based rewards for future healthcare.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

FIG. 3 is a schematic representation of patient medical information obtained from an insurance claim with the doctor's description of the patient's conditions presented as a natural language expression written in a foreign language (Chinese);

FIG. 4 is a schematic representation of the patient medical information of FIG. 3 with the doctor's description of the patient's conditions translated into English;

FIG. 5 is a schematic representation of the patient medical information of FIG. 4 with predetermined codes associated with the patient's conditions;

FIG. 6 is a schematic representation of a health risk profile created based on patient medical data including, among other things, the predetermined codes from FIG. 5;

FIG. 7 is a schematic representation of a second page of the health risk profile shown in FIG. 6;

FIG. 8 is a flowchart generally illustrating more detailed steps of creating a health risk profile for an individual from converted data and additional data;

DETAILED DESCRIPTION

Figure 1:
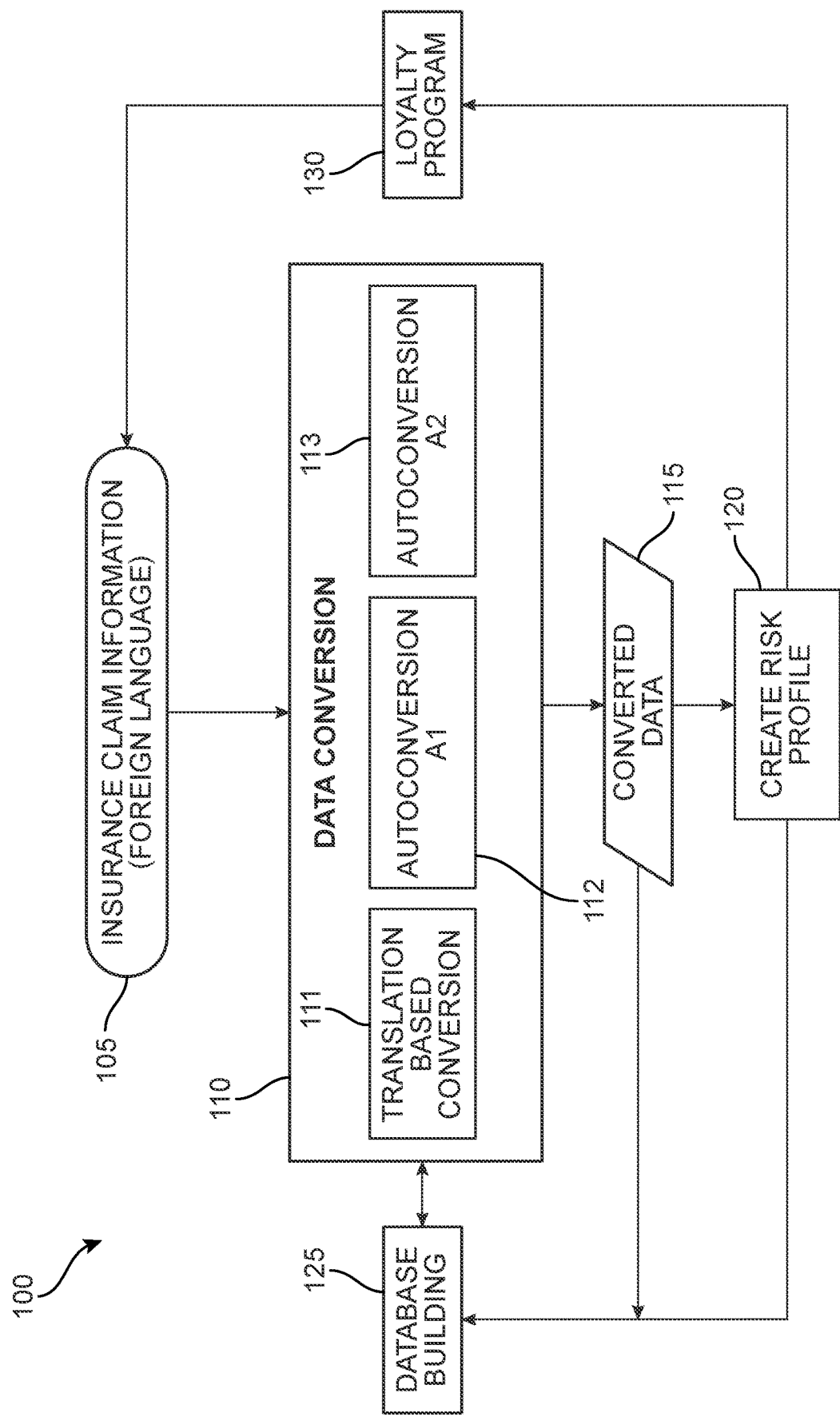
FIG. 1 is a flowchart generally illustrating subroutines of an exemplary disclosed method of determining a health risk profile.

The present disclosure is directed to a system including a processor and a non-transient computer readable medium including instructions for performing a health risk profile determination method. FIG. 1 is a flowchart generally illustrating subroutines of an exemplary disclosed method 100 of determining a health risk profile. Method 100 may be a method for improving the speed of determining a health risk profile associated with a patient.

As shown in FIG. 1, method 100 may include a step of retrieving patient medical information 105 about the patient, wherein the patient medical information is an uncoded natural language expression in a first language. Patient medical information 105 may be retrieved from various sources, such as insurance claim information, as shown in FIG. 1. For example, after a doctor visit, the doctor creates a record of the visit, providing a description of any diagnoses made and any treatments prescribed. In some embodiments of method 100, the first language in which patient medical information 105 is provided may be a non-English language, such as Chinese.

Further, method 100 may also include performing a data conversion procedure 110 in order to convert patient medical information 105 to a usable format from which a risk profile may be determined. As shown in FIG. 1, data conversion procedure 110 may be performed in one of three different ways. For example, a translation based conversion 111 may be performed in some circumstances. In other circumstances, a first autoconversion 112 may be performed. In still other circumstances, a second autoconversion 113 may be performed. That is, method 100 may select between multiple data conversion procedures in order to optimize the procedure.

Data conversion procedure 110 produces converted data 115, which may be further processed, for example, using predictive modeling. Accordingly, method 100 may also involve a step 120 of creating a risk profile, as shown in FIG. 1.

Additional subroutines performed as part of method 100 may include a database building procedure 125 and a loyalty program 130. As shown in FIG. 1, both converted data 115 and one or more indices of the risk profile may be fed back to a database in order to update the information in the database. In some embodiments, the database may be queried before performing data conversion procedure 110 in order to determine which of the data conversion procedures would provide the most desirable converted data 115. In addition, loyalty program 130 may provide patient monitoring, guidance, and incentives based on the patient's health risk profile. These subroutines will be discussed in further detail below.

Figure 2:
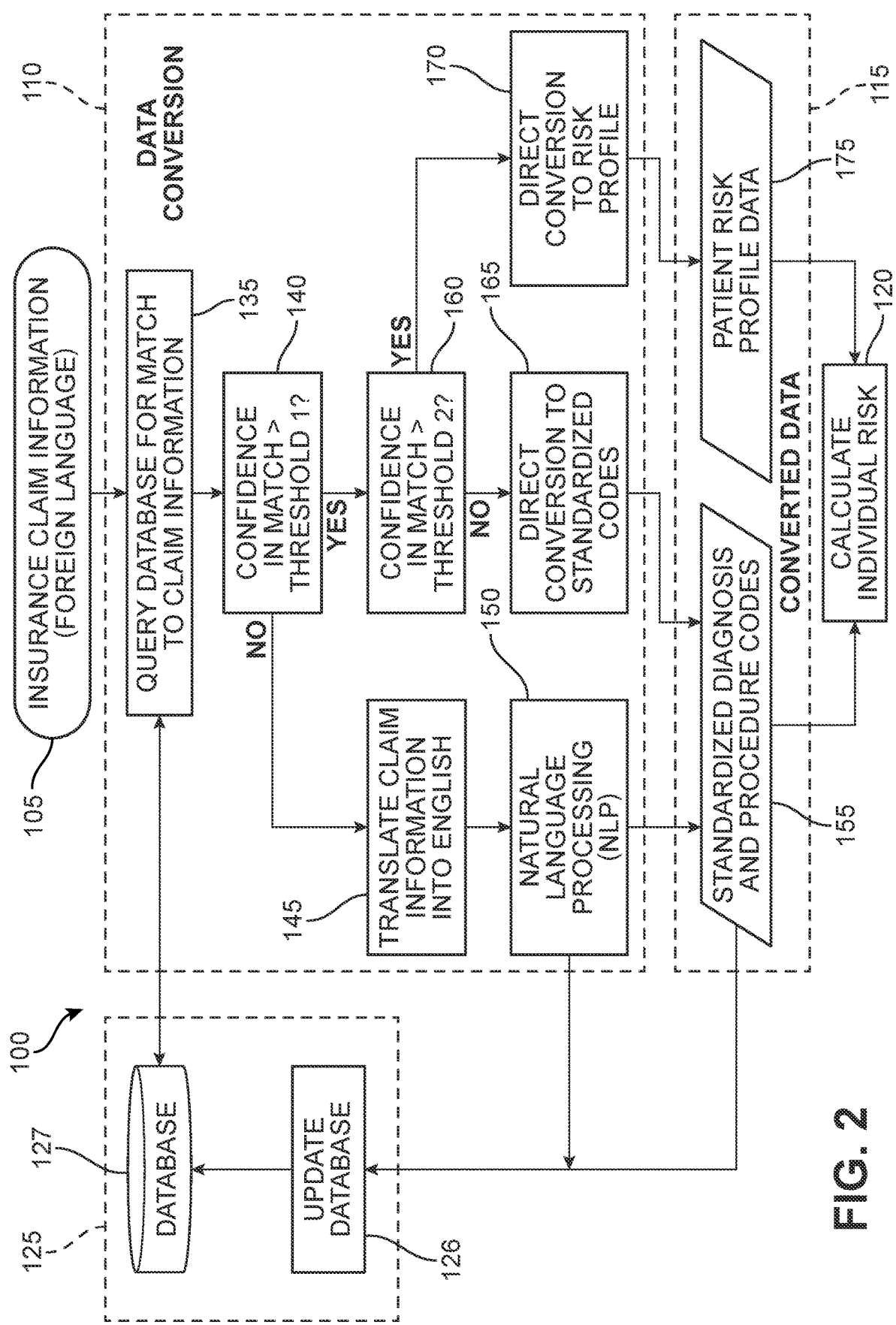
FIG. 2 is a flowchart generally illustrating more detailed steps of a data conversion procedure in the context of the overall method of determining a health risk profile.

FIG. 2 is a flowchart generally illustrating more detailed steps of data conversion procedure 110 in the context of the overall method 100. As shown in FIG. 2, data conversion procedure 110 includes making a query 135 of a database 127. Query 135 involves comparing patient medical information 105 with records in database 127, which includes a plurality of records, wherein at least one record in database 127 has unique preselected medical information and a first predetermined code associated with the preselected medical information. The preselected medical information is also an uncoded natural language expression in the first language, that is, the same language as patient medical information 105. As part of query 135, method 100 may include a step of determining if patient medical information 105 matches one of the records in database 127 by comparing patient medical information 105 with the preselected medical information of the records in database 127.

If the patient medical information matches the preselected medical information, the method includes a step of performing a first data conversion procedure by immediately assigning the first predetermined code associated with the preselected medical information to the patient medical information. If, however, the patient medical information fails to match any record in the first database, then the method involves performing a second data conversion procedure by sending the patient medical information to a translation resource, and receiving translated patient medical information from the translation resource, wherein the translated patient medical information is in a second language; sending the translated patient medical information to a coding resource; and receiving, from the coding resource, a second predetermined code associated with the patient medical information.

That is, if there is a match between the patient medical information and one or more records in the database, then system will use the predetermined code or risk index that the database associates with the predetermined medical information. By using the predetermined code or risk index, the method may skip the translation step. If, however, there is not a match, then the translation step is performed in order to convert the patient medical information from the foreign language to the language of the risk determination system.

Since the patient medical information may not be presented in precisely the same wording as the records in the database, in some embodiments, determining whether there is a match involves evaluating the extent to which the wording of the database record is similar to the patient medical information. In evaluating the extent of the similarity, a level of confidence (a confidence interval) can be determined. For example, the system may determine that there is a database record that the system is 90% confident matches the patient medical information. If that level of confidence exceeds a predetermined threshold, then the system skips the translation step and uses the information in the database to calculate risk.

While the speed of converting the data is important, there is a desire that the converted data be accurate. Accordingly, confidence in the accuracy of the information in the database must exceed a threshold level in order for the system to opt for the faster data conversion procedure. If the level of confidence in the database info exceeds a second, higher threshold level, then not only may the translation step be skipped, but also the step of determining a predetermined standardized code associated with the patient medical information may also be skipped, thus enabling the data conversion procedure to be executed even faster.

As shown in FIG. 2, in step 140, it is determined whether the level of confidence exceeds a first threshold. If not, then method 100 proceeds to step 145 in which patient medical information 105 is translated to a second language, such as English. Next, the translated information may be used to determine predetermined medical codes associated with the patient medical information. Natural language processing 150 may be performed to determine codes 155. Codes 155 may be any standardized codes, such as diagnostic codes and/or procedure codes. For example, in some embodiments, codes 155 may include diagnosis codes selected from the International Classification of Diseases (ICD). In some embodiments, codes 155 may include procedure codes selected from the Current Procedural Terminology (CPT) system.

While the ICD and CPT systems are discussed, any suitable code system may be used. Such code systems may be local, national, or internationally recognized. In addition, more than one code system may be employed in some embodiments. In some cases, separate code systems may be used for diagnoses and procedures, such as the ICD and CPT. In some cases, more than one diagnosis code system may be used and/or more than one procedure code system may be used. In addition, further code systems may be used that are directed to aspects of medical information other than diagnoses and procedures. For example, codes may be standardized for the amount of exercise a patient regularly gets, what age range they fall into, or an assessment of the extent to which the patient eats a healthy diet.

If the level of confidence in the match exceeds the first threshold at step 140, then, at step 160, it may be determined whether the level of confidence exceeds a second, higher threshold. If the higher threshold is not exceeded, then the process proceeds to step 165, which involves performing a direct conversion of patient medical information 105 to standardized, predetermined medical codes 155. If the higher threshold is exceeded, then the process proceeds to step 170, which involves a process of direct conversion of patient medical information 105 to one or more index of a risk profile.

Once one of the three data conversion procedures has been completed on patient medical information 105, the converted data, which may include codes 155 or one or more indices of a risk profile, may be utilized to determine a patient's individual risk at step 120.

FIG. 2 also shows a simplified illustration of database building subroutine 125. As shown in FIG. 2, information from various stages of the overall method can be fed back and used to perform an update to database 127 at step 126. That is, method 100 includes updating database 127 to include a record of an association between the predetermined code (whether determined via the translation-based data conversion procedure or the first autoconversion procedure) and the patient medical information. The information fed back may be simply added to database 127 or, in some embodiments, the accuracy of the information may be checked, for example, by a user of the system. Conclusions as to whether the translated language, the codes, or the patient risk index are accurate may be incorporated into database 127. As the method is continuously run for more and more patients, the database queried at step 135 will be more and more sophisticated. Accordingly, all three of the different data conversion procedures may be performed more effectively the more updated the database becomes. The database-building subroutine is discussed in further detail below.

FIG. 3 is a schematic representation of patient medical information 105. As shown in FIG. 3, patient medical information 105 may be obtained from an insurance claim. As shown in FIG. 3, in some cases, the doctor's description of the patient's conditions may be presented as a natural language expression written in a foreign language, in this case Chinese.

As shown in FIG. 3, patient medical information 105 may include several entries, as reflected in a first column 180. Only two entries are shown in FIG. 3 for the sake of clarity. However, it will be understood that many more line items may be included in patient medical information 105. As also shown in FIG. 3, patient medical information 105 may include an entry ID number reflected in a second column 185. (It will be understood that the order of the columns may vary and the arrangement shown in FIG. 3 is merely exemplary.) In a third column 190, the patient's ID may be reflected. Also, a fourth column 195 shows a data and time that the entry was made. In addition, a fifth column 200 indicates the conditions that the patient was diagnosed with. In FIG. 3, patient ID 1255 was given a first diagnosis 201 and a second diagnosis 202. A sixth column 205 indicates the bill amount for each entry.

As part of the translation based data conversion procedure, the foreign language description may be translated into a second language, such as English. FIG. 4 is a schematic representation of the patient medical information of FIG. 3 with the doctor's description of the patient's conditions translated into English. As shown in FIG. 4, first condition 201 and second condition 202 are no longer represented in Chinese characters. In FIG. 4, first condition 201 is "MIGRAINE" and second condition 202 is "CEREBRAL INFARCTION/COLD."

Once the translation into English is provided, the English description can be matched with an appropriate predetermined medical code. FIG. 5 is a schematic representation of the patient medical information of FIG. 4 with predetermined codes associated with the patient's conditions. Column 210 reflects which code system is being used. In FIG. 5, the code system is reflected as ICD-10-CM. As reflected in column 215, the ICD-10-CM code for "migraine" is G43.909. Column 220 indicates the standard descriptions associated with the ICD-10-CM codes in the respective entry. In particular, a first code description 221 reads "Migraine, unspecified, not intractable, without status, migrainosus." A second code description 222 reads "cerebral infarction, unspecified."

FIG. 6 is a schematic representation of a health risk profile created based on patient medical data including, among other things, the predetermined codes from FIG. 5. FIG. 6 shows a health risk profile 600 for patient ID 1255. Health risk profile 600 is a comprehensive profile prepared based on a relatively large amount of patient medical data, and not only the two entries shown in FIGS. 3-5.

As shown in FIG. 6, health risk profile 600 may include many indices of risk, which may be arranged in various categories. A first category 225 is "Predictive Values." Indices in the Predictive Values category may include "Rank Probability High Total Cost" (235), "Rank Probability High Rx Cost" (240), and "Probability of Persistent High User" (245). These probabilities are represented by a number between 0-1.00. However, any suitable representation of probability may be used. Other probabilities are reflected in a second category 230 "Likelihood of Hospitalization." These probabilities may be calculated based on converted data obtained based on the patient medical information (as converted by any of the three disclosed data conversion procedures), as well as other information and statistical records.

FIG. 7 is a schematic representation of a second page of the health risk profile shown in FIG. 6. As shown in FIG. 7, risk profile 600 may include additional categories. For example, category 605 lists all conditions for which the patient has received prescriptions for medication. In addition, in category 610, the patient's "High Impact Conditions" are listed, in category 615, the patient's "Moderate Impact Conditions" are listed, and in category 620, the patient's "Low Impact Conditions" are listed. The conditions listed in in these categories are examples of groupers. That is, "REN01" is a grouper, meaning the patient has chronic renal failure, and thus, is grouped with other patients having the same condition. All patients categorized under a given grouper have a standard amount added to their risk probabilities (shown in FIG. 6). That is, for two patients having all other data (e.g., age, sex, demographics, etc.) the same, being grouped in REN01 will result in the same risk probability.

In some embodiments, the groupers may be broader categories that encompass multiple diagnoses and/or treatments. For example, there may be only a single grouper for diabetes, even though there are separate diagnoses (and corresponding codes) for type I diabetes and type II diabetes. These separate diagnoses may generally result in the same risk, so they may be categorized under the same grouper to expedite the risk determination process.

FIG. 8 is a flowchart generally illustrating more detailed steps of creating a health risk profile for an individual from converted data and additional data. As shown in FIG. 8, the risk profile (determined at step 120) may be created based on converted data 115, including predetermined medical codes 155. Additionally or alternatively, the risk profile (determined at step 120) may be determined based on risk profile data, as produced, for example, by the second autoconversion procedure discussed above. In addition, the risk profile (determined at step 120) may be created based on additional data 800. Examples of additional data include patient information not necessarily associated with a predetermined medical code, such as sex, age, and weight. In addition, additional data 800 may also include demographics, such as geographic residence of the patient and/or locality of the doctor visit/treatment, as well as socioeconomic information. Further, additional data 800 may include other factors, such as groupers, which may form the basis for grouping patients together for purposes of determining risk profiles.

As shown in FIG. 8, the creation of the risk profile (determined at step 120) may include a step 805 involving categorizing the patients whose risk profiles are being created into one or more risk groups based on commonalities, which may be referred to as "groupers." Examples of groupers include common age, common diagnosis, etc. For instance, in order to determine individual risk, patients having the same condition are grouped together. One or more risk indices may be determined based on the groupings. For example, in some embodiments, all patients in the same "group" may be assigned the same level of risk (e.g., probability) with respect to certain indices.

In addition, in a further step 810, risk may be calculated for multiple parameters/indices. Also, the multiple calculated indices of risk may be collected to create the health risk profile (at step 120). Finally, in a step 815, the method may determine an individual risk profile for each patient.

As discussed above, the disclosed system chooses which data conversion procedure to use depending on the level of confidence in the accuracy of the data in the database. The two autoconversion procedures are faster than the translation based data conversion, as they require fewer steps. Additionally, one or more of the steps of the translation based data conversion procedure that are skipped by the autoconversion procedures may be performed at a remote location, and may not be automated. For example, the translation step 145, the NLP step 150, and the code determination step 151 may be performed at remote locations. Accordingly, by skipping one or more of these steps the autoconversion procedures are much faster and enable the risk profile to be created much faster.

Figure 9:
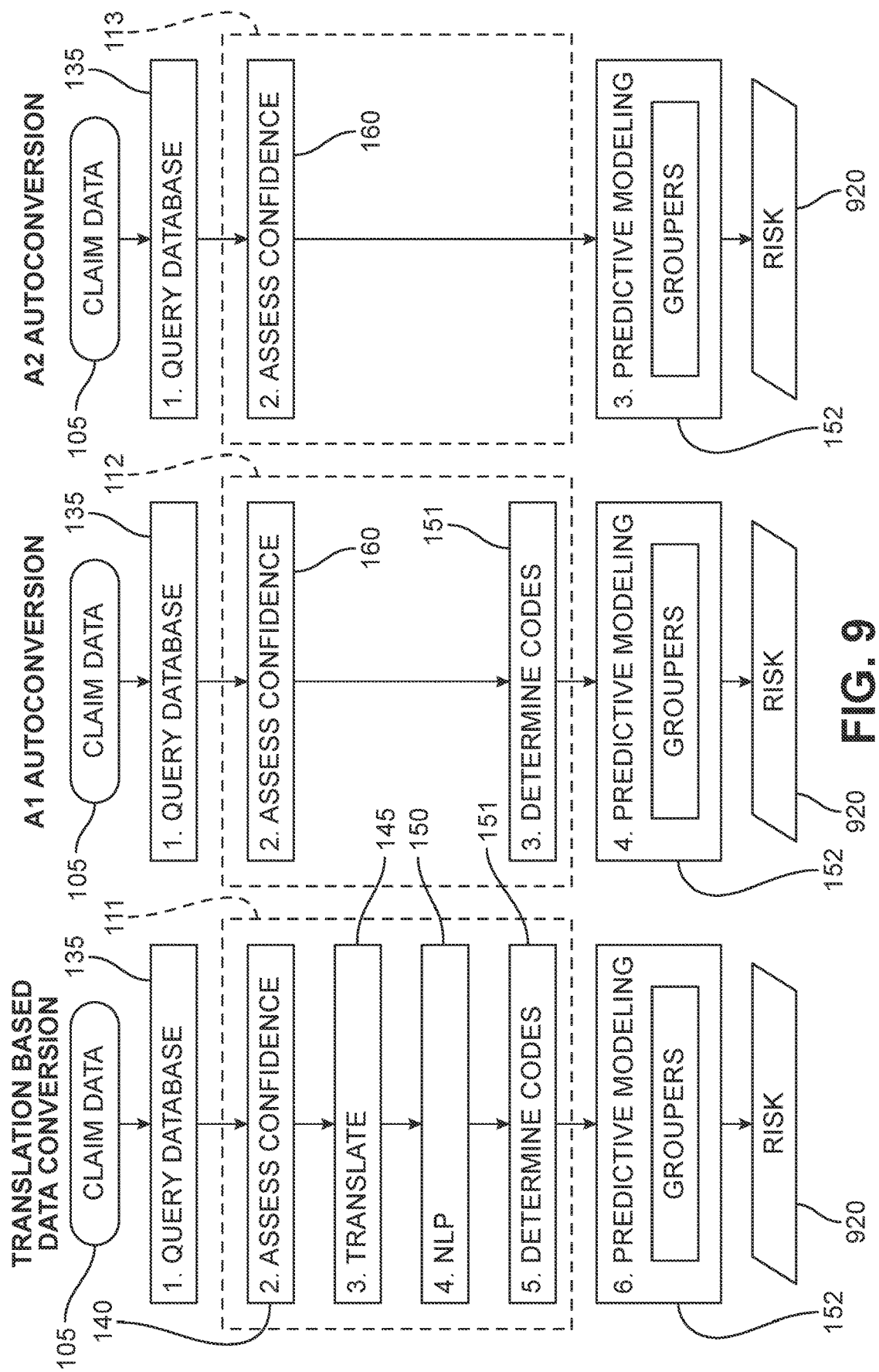
FIG. 9 is a schematic illustration of the health risk profile creation process comparing three different types of data conversion.

FIG. 9 is a schematic illustration of the health risk profile creation process comparing three different types of data conversion. Instead of integrating all three autoconversion procedures into the same flowchart, FIG. 9 shows the full risk creation process with each data conversion procedure for comparison. As shown in FIG. 9, for each of the three risk creation processes, the patient medical information (e.g., claim data) 105 is compared with records in a database by query step 135. Once the query is completed, the data conversion procedure is performed, and the output of the data conversion procedure (i.e., converted data) is subjected to predictive modeling at step 152. As part of the predictive modeling process, the patients may be categorized by groupers. Finally, the risk profile 920 is created.

To the left in FIG. 9, the risk determination process is illustrated with the translation based data conversion procedure 111. As shown in FIG. 9, translation based data conversion procedure 111 includes assessing the confidence level of the database records (step 140), translating the patient medical information (step 145), performing natural language processing (NLP) on the translated data (step 150), and assigning one or more predetermined codes to the translated data (step 151). Thus, the risk determination process includes six general steps when translation based data conversion procedure 111 is used.

The first autoconversion procedure 112 (A1) includes assessing the confidence level of the database records (step 140), and assigning one or more predetermined codes to the translated data (step 151). Accordingly, the risk determination process includes only four steps when using first autoconversion procedure 112. Therefore, when using first autoconversion procedure 112 the risk determination process can be completed much more quickly than when using translation based data conversion 111.

Second autoconversion procedure 113 only includes the step of assessing confidence in the database records (step 160). Accordingly, the risk determination process includes only 3 steps when using second autoconversion procedure 113. Therefore, when using second autoconversion procedure 113, the risk determination process can be performed even more quickly than when using second autoconversion procedure 112.

Figure 10:
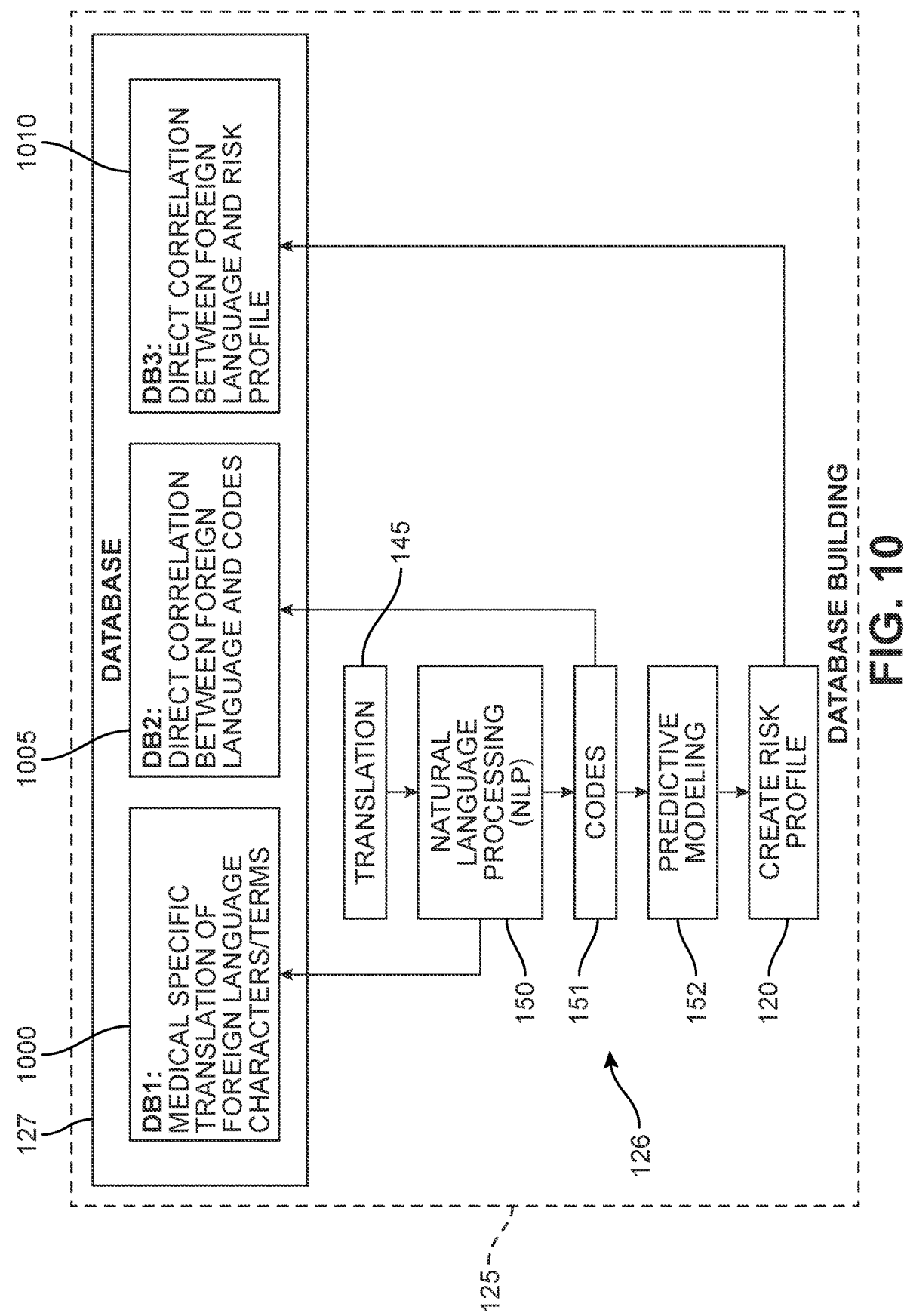
FIG. 10 is a flowchart generally illustrating more detailed steps of building a database according to an exemplary embodiment.

FIG. 10 is a flowchart generally illustrating more detailed steps of database building subroutine 125 shown in FIG. 1. As shown in FIG. 10, database 127 may include several different types of records. In some cases, the records may be stored in separate databases. In other cases, the records may be stored in separate repositories within database 127. As shown in FIG. 10, a DB1 repository 1000 within database 127 may include medical specific translation records. A DB2 repository 1005 within database 127 may include records reflecting a direct correlation between the foreign language in which the patient medical information is presented and the predetermined medical codes assigned to the data. A DB3 repository 1010 within database 127 may include records reflecting a direct correlation between the foreign language in which the patient medical information is presented and indices of the risk profile. Each of these repositories may be updated with feedback at different stages of the overall risk determination method.

As shown in FIG. 10, steps of the overall risk determination method include translation (step 145), natural language processing (step 150), determining codes (step 151), predictive modeling (step 152), and creating the risk profile (step 120). As also shown in FIG. 10, Data produced by natural language processing of translated data (step 145) may be fed back to DB1 repository 1000 to update the translation records. These updated translation records improve the accuracy of future translations and possibly enable expedited data conversion by improving the confidence level of the records in the database. In some cases, the raw translation data, which may be a machine translation or a manual translation, may be fed back to database 127. In other cases, the translation data may be manually reviewed and the records in database 127 may be updated to reflect the outcome of the review process.

As also shown in FIG. 10, the codes assigned to a given set of patient medical information may be fed back to DB2 repository 1005 in order to update the records therein. Accordingly, once the data conversion process has been completed for a given set of patient medical information, the database will then store the results of the data conversion. Accordingly, DB2 repository 1005 will be updated to include records that reflect the direct association between the foreign language patient medical information and the predetermined code with which it corresponds.

In addition, as shown in FIG. 10, data from the final risk profile may be fed back to DB3 repository 1010. While the risk profile may include many data points, associations between certain indices and certain patient medical information may be consistent. For example, it may be determined that the probability of a high total cost for a person with migraines may consistently be determined to be 0.08. Accordingly, once DB3 repository 1010 has been updated with enough records correlating migraines with a high total cost probability of 0.08, the system can bypass the translation and natural language processing steps and directly associate the foreign language term for migraine with a high total cost probability of 0.08. By eliminating the steps, the high total cost probability of 0.08 can be determined much more quickly.

These databases may be maintained on-site on a local server, or they may be accessed through a proxy gateway which will treat a database located on an external service provider's server as if it were a local database.

Figure 11:
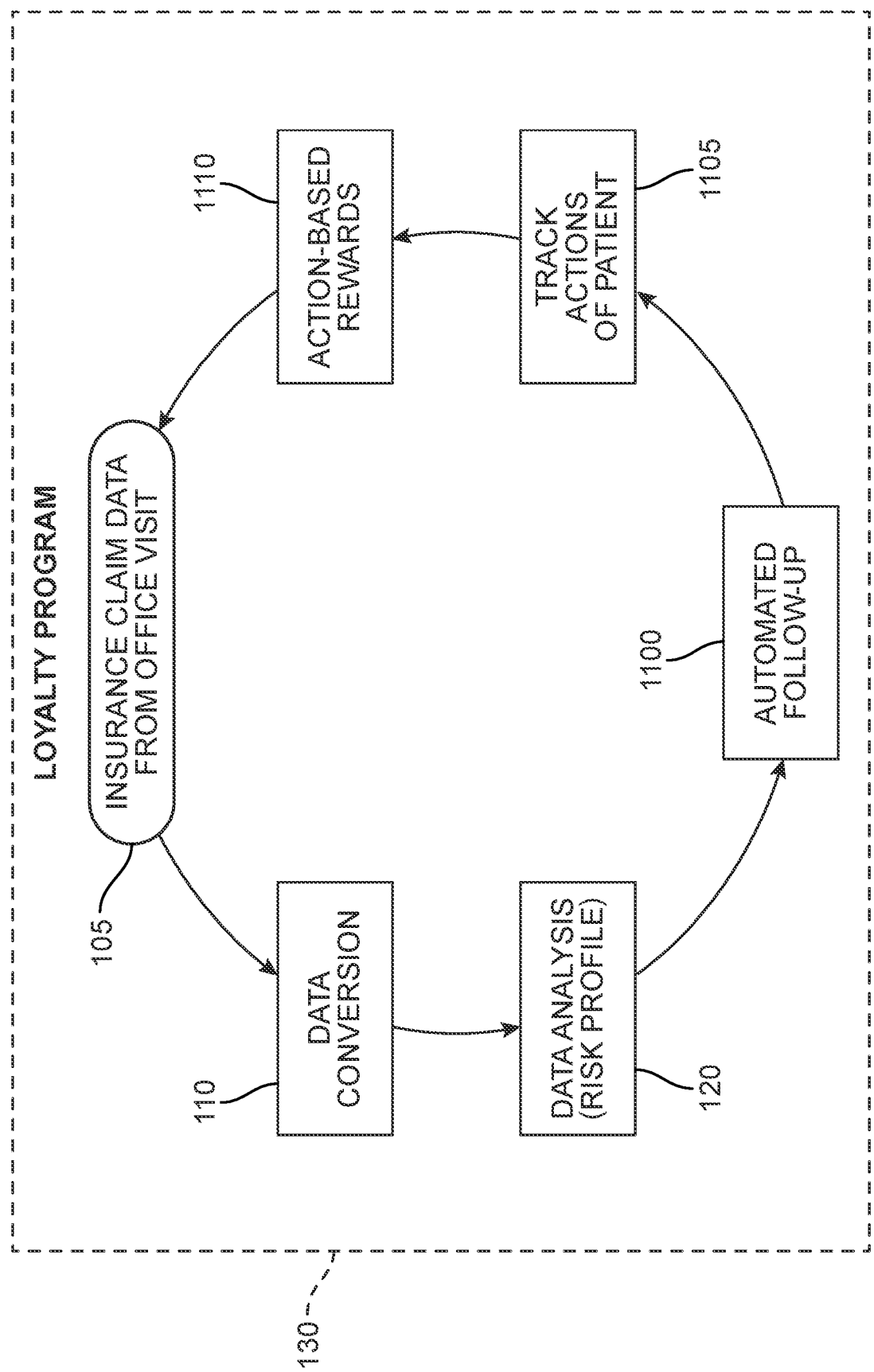
FIG. 11 is a flowchart generally illustrating more detailed steps of a loyalty program according to an exemplary embodiment.

FIG. 11 is a flowchart generally illustrating more detailed steps of loyalty program 130. Once data conversion 110 is completed to facilitate creation of a health risk profile (step 120), an automated follow-up 1100 may be performed to check in on the patient. For example, following an office visit, the data from the office visit may be converted and analyzed to determine a risk profile. Using one or more indices from the risk profile, the system may perform a follow-up with the patient, e.g., to remind them to schedule a follow-up appointment or to pick up a prescription. Further, the system may track the actions of the patient (step 1105) and provide action-based rewards (step 1110) to the patient. For example, post appointment actions may be tracked, such as whether the patient picks up a prescription, attends prescribed therapy sessions, pays their bill on time, etc. Based on these tracked actions, rewards may be awarded to the patient, such as a coupon for a future office visit or other incentives for choosing a particular provider or service.

Figure 12:
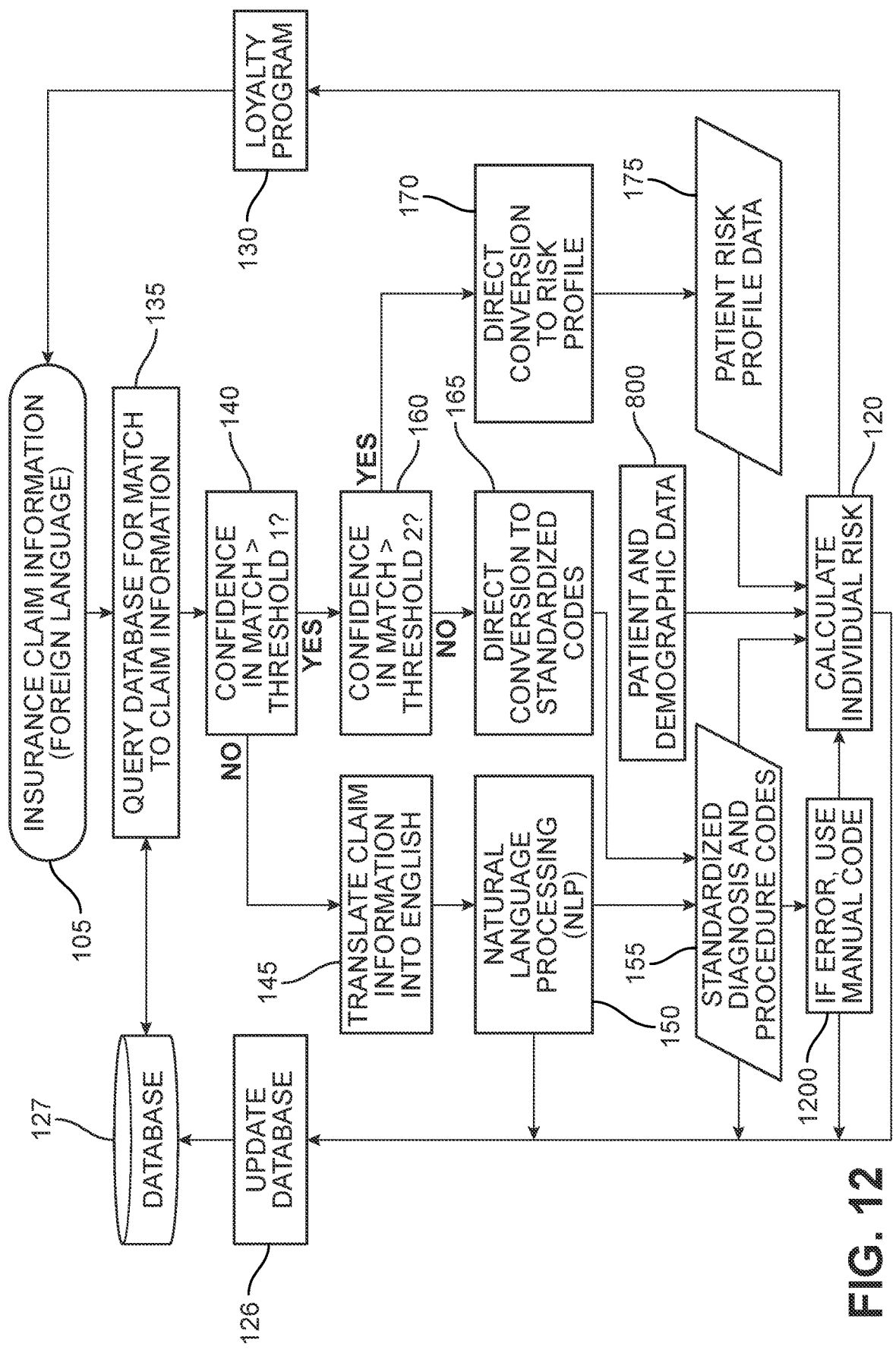
FIG. 12 is a flowchart generally illustrating the method depicted in FIG. 1 expanded to show additional steps within select subroutines.

FIG. 12 is a flowchart generally illustrating the method depicted in FIG. 1 expanded to show additional steps within select subroutines. FIG. 12 includes certain steps shown in FIG. 2, and incorporates additional steps. It will be understood that not every step of the overall risk calculation process is shown in FIG. 12 in order to ensure clarity. FIG. 12 illustrates two additional aspects of the process. In particular, FIG. 12 illustrates the consideration of patient and demographic data 800 in the risk profile determination. (See FIG. 8 for further details regarding additional patient and demographic data 800.)

In addition, FIG. 12 also shows an error resolution step 1200. In error resolution step 1200, the system accounts for certain discrepancies between the healthcare practices in the patient's locality and the healthcare practices elsewhere. For example, certain healthcare practices that may be considered "alternative medicine" or "holistic medicine" by certain western societies may be mainstays of certain eastern societies. For example, in traditional Chinese medicine, symptoms of various illnesses are believed to be either the product of disrupted, blocked, and unbalanced qi (pronounced "chi") movement through meridians or deficiencies and imbalances of qi. Traditional Chinese medicine often seeks to relieve these imbalances by adjusting the circulation of qi using a variety of techniques including herbology, food therapy, physical training regimens (e.g., martial arts), moxibustion, tui na, or acupuncture.

Diagnoses and treatments related to qi may not be well-covered by codes in an international medical code system. In such cases, the process of determining predetermined codes for these diagnoses and treatments may produce errors. In order to resolve such errors, a code may be assigned to the these diagnoses and treatments according to a different protocol. For example, in some cases, a best-fit code may be assigned. That is, from the code system, the code that best fits the alternative medicine data may be selected. Alternatively, a new, custom code may be assigned that was not part of the standardized system initially. The best-fit code or custom code may be used to complete the creation of the individual risk profile.

In some embodiments, the best-fit codes and/or the custom codes may be assigned manually by a user of the system. In some embodiments, the best-fit codes and/or the custom codes may be selected automatically according to a predetermined protocol. As shown in FIG. 12, the database may be updated with information about the diagnoses and treatments having no counterparts in the code system. For example, any best-fit codes and custom codes assigned to such medical information may be added to the database. These database updates will improve and expedite the process of determining health risk based on such diagnoses and treatments.

Figure 13:
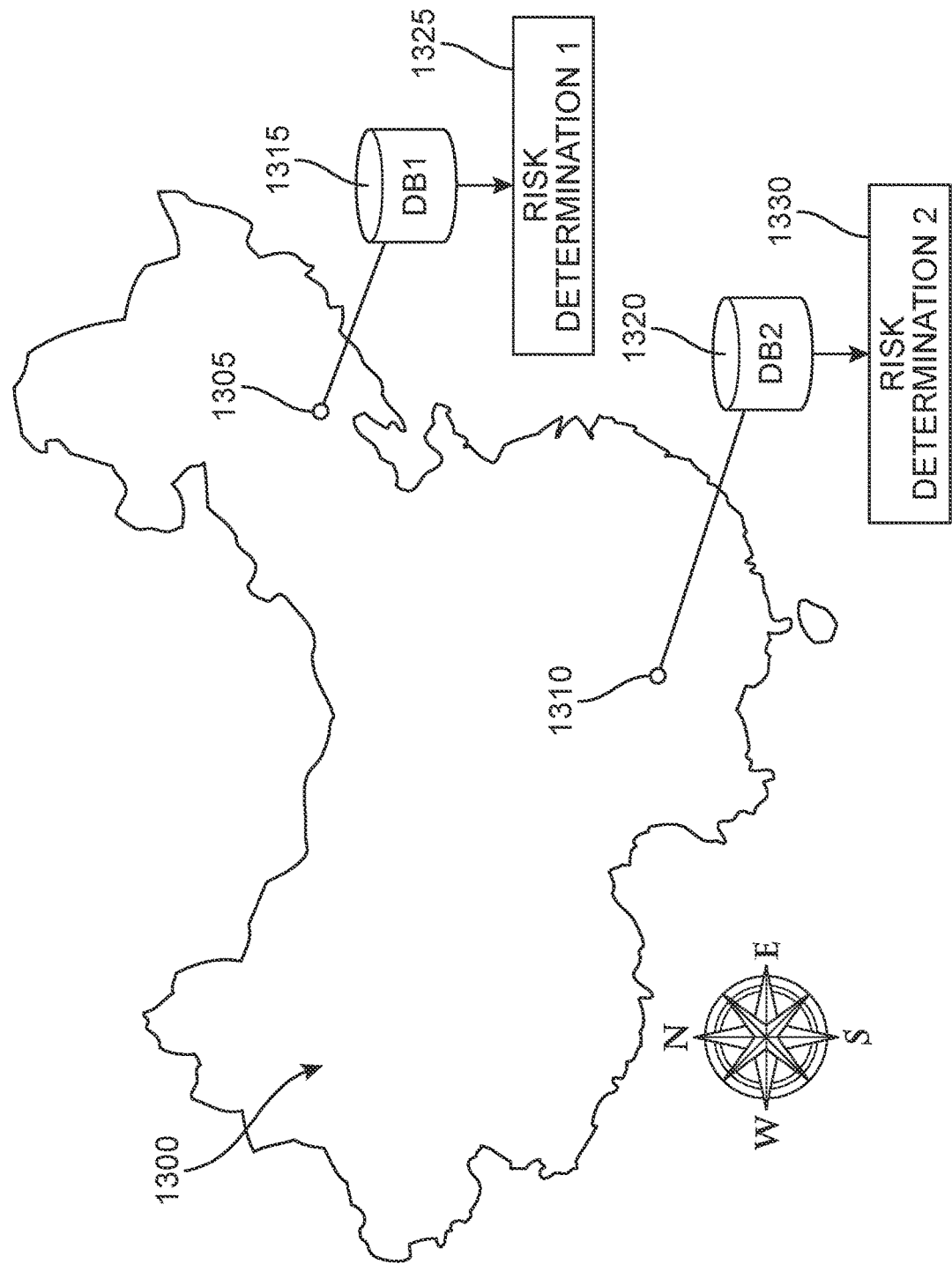
FIG. 13 is a schematic diagram illustrating that risk determination can vary from one geographic locality to another.

In some embodiments, the risk profile may differ depending on the demographics information considered. Accordingly, the risk indices may vary from one geographic region to another. FIG. 13 illustrates a map of a country 1300. For purposes of illustration, country 1300 is shown as an outline of China. Two different geographic localities within country 1300 are identified in FIG. 13 and may be associated with different databases. In particular, a first region 1305 is associated with a first database 1315, whereas a second region 1310 of country 1300 is associated with a second database 1320. Because demographic data for patients who live or attend a physician in first locality 1305 may differ from the demographic data for patients who live or attend a physician in second locality 1310, the risk determined for patients in the two localities may differ. Accordingly, a first risk determination 1325 based on records and information in first database 1315 may produce a different risk profile than a second risk determination 1330 performed based on records and information in second database 1320. This may enable more accurate risk profiles to be created for individual patients.

Figure 14:
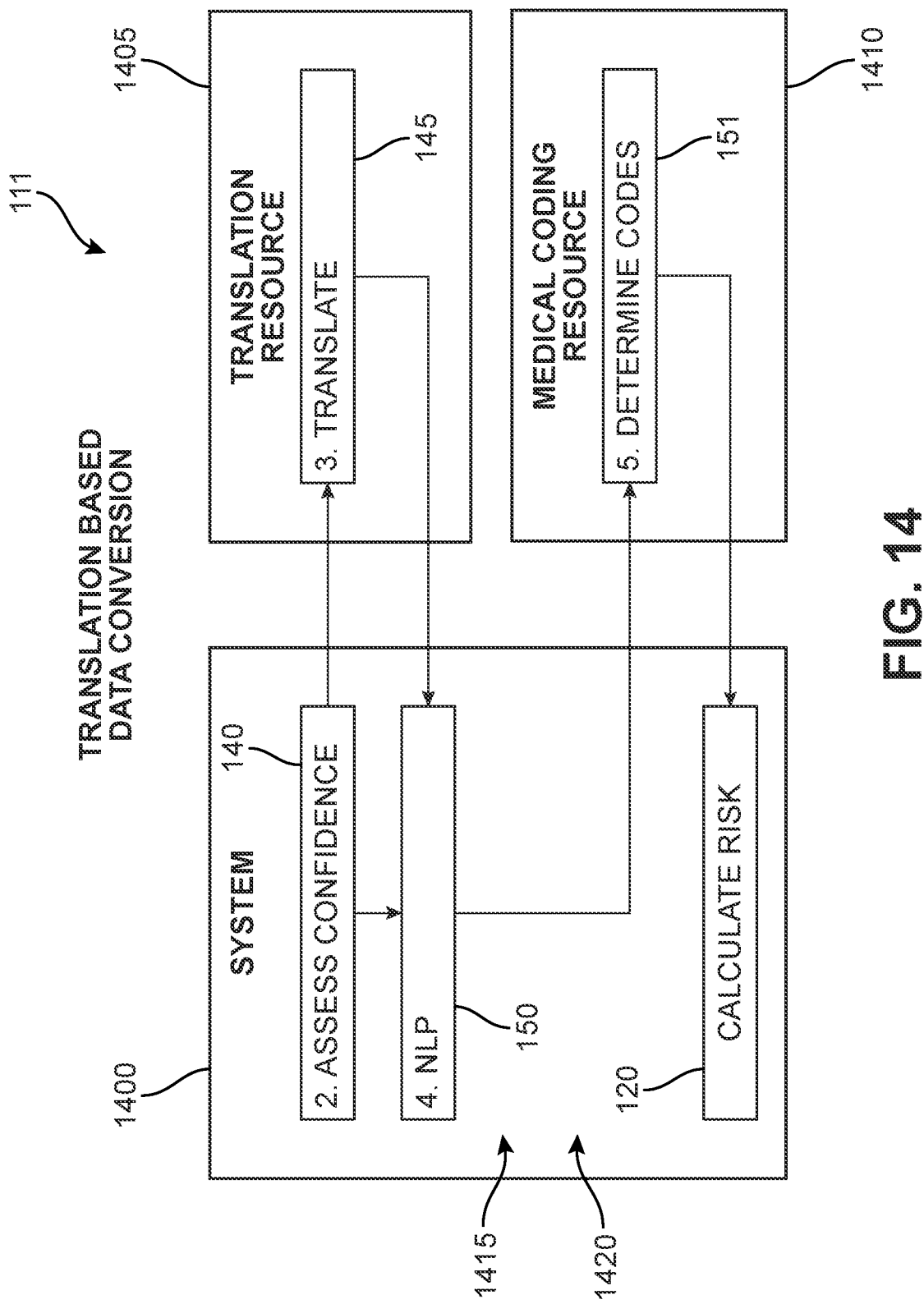
FIG. 14 is a schematic block diagram illustrating components and functions executed when performing a translation based data conversion.

As discussed above, in some cases, certain steps of the data conversion process may be performed in a remote location. FIG. 14 is a schematic block diagram illustrating components and functions executed when performing a translation based data conversion 111. As shown in FIG. 14, the methods discussed above may be performed by a system 1400. System 1400 may include a processor 1415 and a non-transient computer readable medium 1420 including instructions for performing the disclosed method steps. System 1400 may include or reside within a server. Non-transient computer readable medium 1420 may include magnetic disks, optical discs, a memory, or other storage device. Processor 1415 may be configured to execute the instructions stored in non-transient computer readable medium 1420.

As also shown in FIG. 14, translation step 145 may be performed by a translation resource 1405, which may be at a different location than system 1400. Translation resource 1405 may provide automated and/or manual translation services. Therefore, not only does translation step 145 add time to the risk determination process, in some cases, it may add a significant amount of time while the translation is performed manually.

In some cases, the assignment of codes to the translated patient medical information may be performed by a medical coding resource 1410. In some embodiments, medical coding resource 1410 and translation resource 1405 may be different resources, and may be provided in different locations, as shown in FIG. 14. Accordingly, after translation step 145 is complete, the translation data may be returned to system 1400 for natural language processing 150. Then, after natural language processing 150 has been completed, the data may be sent to medical coding resource 1410 in a remote location. After the coding has been completed, the codes may be sent back to system 1400 for calculation of risk (step 120).

In some cases, translation resource 1405 and/or medical coding resource 1410 may be located a significant distance from system 1400. In some cases, certain restrictions, such as regulations, licenses, language barriers, etc. may limit translation resource 1405 and/or medical coding resource 1410 to certain localities. Accordingly, in some instances, one or both of these resources may be located in a different country or countries from system 1400. In such cases, the data may be transferred back and forth between system 1400 and the resources via the Internet, or other means of data transfer.

As shown in FIG. 14, of the five general steps of translation based data conversion procedure 111, two of these steps are performed by remote resources. This can slow down the data conversion process, and thus, the creation of a risk profile.

Figure 15:
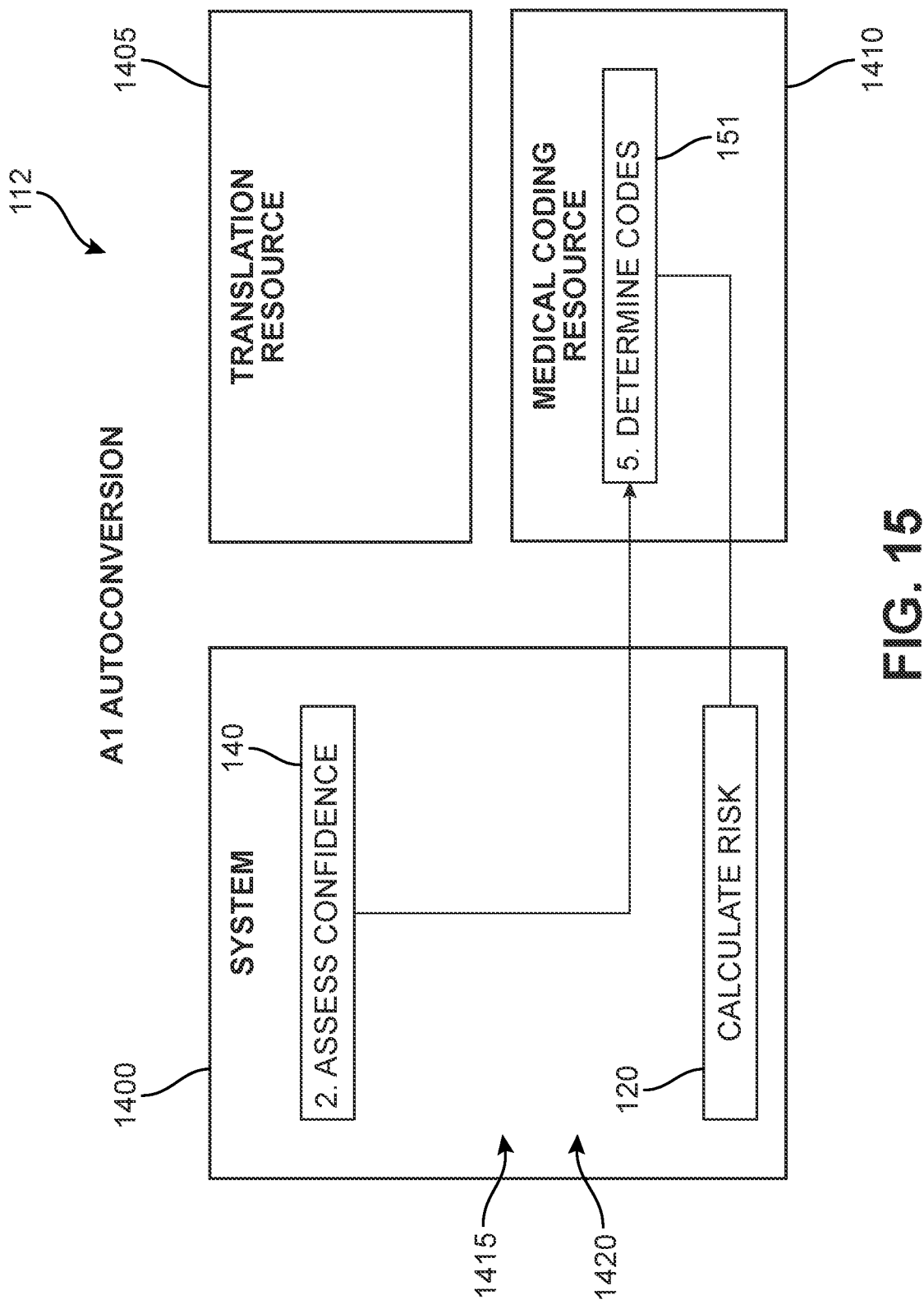
FIG. 15 is a schematic block diagram illustrating components and functions executed when performing a first data autoconversion procedure.

FIG. 15 is a schematic block diagram illustrating components and functions executed when performing first data autoconversion procedure 112. As shown in FIG. 15, although the translation step is skipped by first data autoconversion procedure 112, the coding step 151 may still be outsourced to medical coding resource 1410. Accordingly, because the data need not be sent to and received from translation resource 1405 for first data autoconversion procedure 112, this procedure can be completed much more quickly than translation based data conversion procedure 111.

Figure 16:
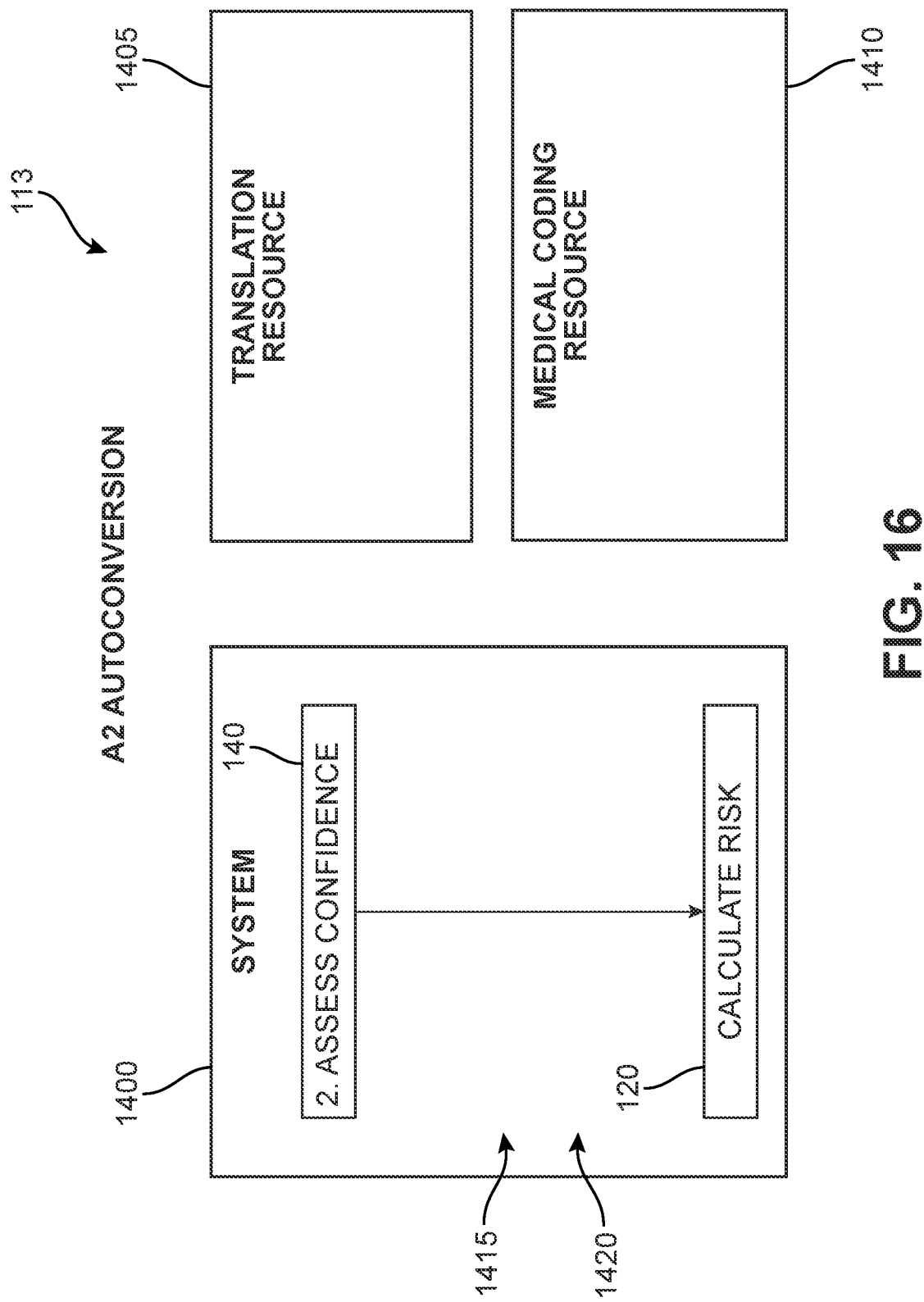
FIG. 16 is a schematic block diagram illustrating components and functions executed when performing a second data autoconversion procedure.

FIG. 16 is a schematic block diagram illustrating components and functions executed when performing second data autoconversion procedure 113. As shown in FIG. 16, after assessing the confidence level (step 140), system 1400 may convert the patient medical data directly to risk indicia. Accordingly, since the translation step and the coding step are skipped altogether, the data never needs to leave system 1400. Therefore, second autoconversion procedure 113 may be completed more quickly than first autoconversion procedure 112 and much more quickly than translation based conversion procedure 111.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A method for improving the speed of determining a health risk profile associated with a patient comprising the steps of:
using a device processor to execute instructions stored on a non-transitory computer readable medium to perform the following steps:
retrieving patient medical information about the patient, wherein the patient medical information is an uncoded natural language expression in a first natural language;
comparing the patient medical information with records in a first database, the first database including a plurality of records, wherein at least one record in the first database has preselected medical information and a first predetermined code associated with the preselected medical information, and wherein the preselected medical information is also an uncoded natural language expression in the first natural language;
determining if the patient medical information matches one of the records in the first database by comparing the patient medical information with the preselected medical information of the records in the first database;
if the patient medical information matches the preselected medical information, performing a first data conversion procedure by immediately assigning the first predetermined code associated with the preselected medical information to the patient medical information; and
if the patient medical information fails to match any record in the first database, performing a second data conversion procedure more slowly than the first data conversion procedure by, sending the patient medical information to a translation resource, and receiving translated patient medical information from the translation resource, wherein the translated patient medical information is in a second natural language different than the first natural language; sending the translated patient medical information to a coding resource; and receiving, from the coding resource, a second predetermined code associated with the patient medical information; and
determining a health risk profile for the patient using one of the first predetermined code and the second predetermined code;
the method further including making a determination of a level of confidence that the patient medical information matches the preselected medical information;
wherein determining if the patient medical information matches one of the records in the first database is perforated by determining whether the level of confidence exceeds a first predetermined non-zero threshold; and
wherein, if the level of confidence exceeds a second predetermined threshold that is higher than the first predetermined threshold, the method further includes performing a third data conversion procedure by immediately assigning a first health risk index associated with the preselected medical information to the patient medical information; and determining a health risk profile for the patient using the first health risk index.

2. The method of claim 1, wherein the first predetermined code is a diagnosis code.

3. The method of claim 1, wherein the first predetermined code is a procedure code.

4. The method of claim 1, further including updating the first database to include a record of an association between the second predetermined code and the patient medical information.

5. The method of claim 1, further including:
performing an assessment to verify the accuracy of at least one of the translated patient medical information from the translation resource and the second predetermined code associated with the patient medical information.

6. The method of claim 5, further including using results of the assessment to update the first database.

7. The method of claim 1, further including a step of producing an automated follow-up with a patient based on the health risk profile.

8. The method of claim 1, further including a step of tracking actions of a patient following an office visit and providing the patient with action-based rewards for future healthcare.

9. A system for improving the speed of determining a health risk profile associated with a patient comprising:
a processor; and
a non-transient computer readable medium including instructions for performing the following steps:
retrieving patient medical information about the patient, wherein the patient medical information is an uncoded natural language expression in a first natural language;
comparing the patient medical information with records in a first database, the first database including a plurality of records, wherein at least one record in the first database has unique preselected medical information and a first predetermined code associated with the preselected medical information and wherein the preselected medical information is also an uncoded natural language expression in the first natural language;
determining if the patient medical information matches one of the records in the first database by comparing the patient medical information with the preselected medical information of the records in the first database;
if the patient medical information matches the preselected medical information, performing a first data conversion procedure by immediately assigning the first predetermined code associated with the preselected medical information to the patient medical information;
if the patient medical information fails to match any record in the first database, performing a second data conversion procedure more slowly than the first data conversion procedure by sending the patient medical information to a translation resource, and receiving translated patient medical information from the translation resource, wherein the translated patient medical information is in a second natural language different than the first natural language; sending the translated patient medical information to a coding resource; and receiving, from the coding resource a second predetermined code associated with the patient medical information; and determining a health risk profile for the patient using one of the first predetermined code and the second predetermined code;

wherein the non-transient computer readable medium further includes instructions for making a determination of a level of confidence that the patient medical information matches the preselected medical information;

wherein the non-transient computer readable medium further includes instructions for determining if the patient medical information matches one of the records in the first database is performed by determining whether the level of confidence exceeds a first predetermined non-zero threshold; and wherein, if the level of confidence exceeds a second predetermined threshold that is higher than the first predetermined threshold, the method further includes performing a third data conversion procedure by immediately assigning a first health risk index associated with the preselected medical information to the patient medical information; and determining a health risk profile for the patient using the first health risk index.

10. The system of claim 9, wherein the predetermined code is a diagnosis code.

11. The system of claim 9, wherein the predetermined code is a procedure code.

12. The system of claim 9, wherein the non-transient computer readable medium further includes instructions for updating the first database to include a record of an association between the second predetermined code and the patient medical information.

* * * * *

UNITED STATES PATENT AND TRADEMARK OFFICE
CERTIFICATE OF CORRECTION

PATENT NO. : 11,830,626 B2
APPLICATION NO. : 17/175007
DATED : November 28, 2023
INVENTOR(S) : Henry H. Cha Page 1 of 1

It is certified that error appears in the above-identified patent and that said Letters Patent is hereby corrected as shown below:

In the Claims

In Claim 1, Line 30 (Column 15, Line 44), "by, sending" is replaced with --by sending--

In Claim 9, Line 15 (Column 16, Line 43), "information and" is replaced with --information, and--

In Claim 9, Line 40 (Column 17, Line 1), "resource a" is replaced with --resource, a--

In Claim 9, Line 54 (Column 17, Line 16), "is performed" is deleted.

Signed and Sealed this
Second Day of January, 2024

Katherine Kelly Vidal
*Director of the United States Patent and Trademark Office*